United States Patent [19]

Castella Sola et al.

[11] Patent Number: 5,245,091
[45] Date of Patent: Sep. 14, 1993

[54] PROCESS FOR THE PREPARATION OF 1,1-BIS(CHLOROPHENYL)-2,2,2-TRICHLOROETHANOL

[75] Inventors: Jaume Castella Sola; Jaime Palencia Adrubau, both of Badalona, Spain; Raymond Commandeur, Vizille; Bernard Gorny, Echirolles, both of France

[73] Assignee: Elf Atochem S.A., Puteaux, France

[21] Appl. No.: 834,250

[22] PCT Filed: Jun. 20, 1991

[86] PCT No.: PCT/FR91/00495

§ 371 Date: Apr. 20, 1992

§ 102(e) Date: Apr. 20, 1992

[87] PCT Pub. No.: WO92/00264

PCT Pub. Date: Jan. 9, 1992

[30] Foreign Application Priority Data

Jun. 22, 1990 [FR] France ............................. 90 07849

[51] Int. Cl.$^5$ ............................................. C07C 33/46
[52] U.S. Cl. ........................................ 568/812; 568/715
[58] Field of Search ............................... 568/715, 812

[56] References Cited

U.S. PATENT DOCUMENTS

| | | | |
|---|---|---|---|
| 2,812,280 | 11/1957 | Wilson | 568/812 |
| 2,812,362 | 11/1957 | Wilson | 568/812 |
| 2,812,365 | 11/1957 | Wilson et al. | 568/812 |
| 2,932,672 | 4/1960 | Miller et al. | 568/810 |
| 4,705,902 | 11/1987 | Nichols | 568/812 |
| 5,075,512 | 12/1991 | Adrubau et al. | 568/810 |
| 5,081,319 | 1/1992 | Adrubau et al. | 568/810 |
| 5,118,881 | 6/1992 | Vaubuch et al. | 568/810 |

FOREIGN PATENT DOCUMENTS

| | | | |
|---|---|---|---|
| 248954 | 12/1987 | European Pat. Off. | 568/812 |
| 409689 | 1/1991 | European Pat. Off. | 568/812 |
| 1034684 | 7/1953 | France | 568/812 |
| 831421 | 3/1960 | United Kingdom | 568/812 |

OTHER PUBLICATIONS

Tomar et al, "Chemical Abstracts," vol. 81 (Nov. 25–Dec. 9, 1974) p. 151778h.

Primary Examiner—Werren B. Lone
Attorney, Agent, or Firm—Burns, Doane, Swecker & Mathis

[57] ABSTRACT

The invention relates to a process for the synthesis of 1,1-bis(chlorophenyl)-2,2,2-trichloroethanol in (dicofol) from chlorol and chlorobenzene, in which process the acid by-products formed during the condensation reaction of the chloral and the chlorobenzene are used as reaction medium in the final step for synthesis of dicofol.

11 Claims, No Drawings

PROCESS FOR THE PREPARATION OF 1,1-BIS(CHLOROPHENYL)-2,2,2-TRICHLOROETHANOL

The present invention relates to a process for the preparation of 1,1-bis(chlorophenyl)-2,2,2-trichloroethanol. This product, usually termed "dicofol", is useful as a pesticide.

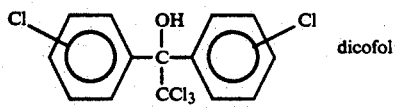 dicofol

To date, dicofol has been synthesised from DDT, which is also a pesticide.

Crystalline 1,1-bis(chlorophenyl)-2,2,2-trichloroethane (DDT) is melted and is then converted

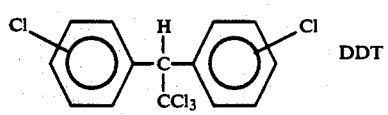 DDT to 1,1-bis(chlorophenyl)-1,2,2,2-tetrachloroethane (chloro-DDT), either by chlorination or by a dehydrochlorination followed by an addition of chlorine, and the chloro-DDT is then hydrolysed to dicofol in the presence of sulphuric acid and a sulphonic acid. This process is mentioned in the introduction of European Patent EP No. 0,409,689 and U.S. Pat. No. 4,705,902. U.S. Pat. Nos. 2,812,280 and 2,812,362 describe the hydrolysis of chloro-DDT to dicofol. After hydrolysis, a solvent is added and an organic phase containing crude dicofol and an aqueous phase containing sulphuric acid and sulphonic acid are thus obtained. This aqueous phase may be re-used only once for the hydrolysis of chloro-DDT or dicofol. In fact, it has been found that it became loaded with impurities which interfered in the hydrolysis. The sulphonic acid may be benzenesulphonic acid, para-toluenesulphonic acid or butylbenzenesulphonic acid. This acid phase is not usable as such. It is necessary to desulphonate it by means of steam in order to produce residual sulphuric acid and benzene, toluene or butylbenzene. It is thus possible to recover benzene, toluene or butylbenzene of good purity and residual sulphuric acid, which may be used in applications where it is not necessary to have a pure acid. It then suffices to sulphonate the benzene, toluene or butylbenzene in order to reproduce a solution of sulphuric acid and sulphonic acid necessary for the hydrolysis of chloro-DDT.

Moreover, this process requires the handling of DDT in solid form in order to dissolve it in tetrachloroethane or in methanol (examples 2 and 3 of U.S. Pat. No. 2,812,280). In fact, DDT is most often supplied in solid form, as tablets.

A very much simpler process for the preparation of dicofol has now been found which avoids the handling of DDT and the losses of DDT in the for of dust and which avoids the preparation of a solution of sulphuric acid and sulphonic acid and also gives a better yield.

The invention is a process for the synthesis of 1,1-bis(-chlorophenyl)-2,2,2-trichloroethanol, in which:

(a) chloral is reacted with an excess of chlorobenzene in the presence of sulphuric acid;

(b) an aqueous phase containing sulphuric acid and para-chlorobenzenesulphonic acid and an organic phase consisting of 1,1-bis(chlorophenyl)-2,2,2-trichloroethane in solution in chlorobenzene are obtained;

(c) the 1,1-bis(chlorophenyl)-2,2,2-trichloroethane is converted to 1,1-bis(chlorophenyl)-1,2,2,2-tetrachloroethane;

(d) the 1,1-bis(chlorophenyl)-1,2,2,2-tetrachloroethane is hydrolysed to 1,1-bis(chlorophenyl)-2,2,2-trichloroethanol in the presence of all or some of the aqueous acid phase of step (b);

(e) at the end of step (d), chlorobenzene is added and an organic phase consisting of 1,1-bis(chlorophenyl)-2,2,2-trichlorethanol in solution in chlorobenzene and an aqueous phase containing sulphuric acid and para-chlorobenzenesulphonic acid are thus obtained; and (f) the acid aqueous phases originating from steps (b) and (e) are distilled by entrainment in steam to give (i) chlorobenzene, which is recycled, and (ii) residual sulphuric acid.

The principle of the reaction of step (a) is known. It has been described in U.S. Pat. No. 2,932,672. "In the presence of sulphuric acid" implies that it is possible to have any concentration, including the acid in the form of oleum. The condensation reaction of chlorobenzene with chloral is preferably carried out at between −20° and −15° C. The reaction mixture is then heated to about 40° to 75° C. and, if necessary further chlorobenzene is added until two phases are obtained an organic phase consisting of chlorobenzene and containing all of the 1,1-bis(chlorophenyl)-2,2,2-trichloroethane and an aqueous phase containing sulphuric acid and para-chlorobenzenesulphonic acid. Water is formed by the condensation reaction of chlorobenzene with chloral. Para-Chlorobenzenesulphonic acid has formed by the action of the sulphuric medium on chlorobenzene. Those skilled in the art are able to adjust the excess of chlorobenzene in order to obtain these two phases, one organic and the other aqueous. The aqueous phase may be washed with chlorobenzene in order to be certain to properly extract all of the 1,1-bis(chlorophenyl)-2,2,2-trichloroethane. This chlorobenzene may be re-used in step (a).

The organic phase may be washed with water or with water containing sodium carbonate.

The conversion, in step, (c), of 1,1-bis(chlorophenyl)-2,2,2-trichloroethane to 1,1-bis(chlorophenyl)-1,2,2,2-tetrachloroethane may be carried out by any means. That is to say it is possible to dehydrochlorinate and then to chlorinate or to chlorinate directly. The principle of these reactions is known per se.

On the other hand, the Applicant has found that it was no longer necessary to proceed via 1,1-bis(chlorophenyl)-2,2,2-trichloroethane in the solid state.

According to the present invention, step (c) may be carried out directly on the organic phase obtained in step (b).

The procedure used may be the same as that described in Examples 2 and 3 of U.S. Pat. No. 2,812,280, but using chlorobenzene in place of tetrachloroethane or methanol as the solvent for 1,1-bis(chlorophenyl)-2,2,2-trichloroethane.

According to a preferred form of the invention, the chlorobenzene is removed from the organic phase from step (b) by steam distillation at between 90° and 110° C. 1,1-bis(chlorophenyl)-2,2,2-trichloroethane is then obtained in the molten state and a dehydrochlorination is then carried out with the aid of an aqueous alkaline solution. An organic phase is obtained which consists of 1,1-bis(chlorophenyl)-2,2-dichloroethylene and an alkaline aqueous phase.

1,1-bis(chlorophenyl)-2,2-dichloroethylene is subjected to bulk chlorination in order to produce 1,1-bis(chlorophenyl)-1,2,2,2-tetrachloroethane.

The principle of step (d) of the process of the invention is known per se. The Applicant has found that by using all or part of the acid aqueous phase originating from step (b), a better yield of dicofol is surprisingly obtained. That is to say, the amount of 1,1-bis(chlorophenyl)-2,2,2-trichloroethanol represents 87 to 88% by weight of the product obtained in step (e) (outside of chlorobenzene), whereas if dicofol is produced from 1,1-bis(chlorophenyl)-2,2,2-trichloroethane using an acidic aqueous phase, which does not originate from the synthesis in step (a) the amount falls from 87/88% to 85/86%.

In addition to this advantage, a better yield based on the use chloral is also obtained.

It was known, following the hydrolysis reaction of step (d), to add a solvent in order to extract the 1,1-bis(chlorophenyl)-2,2,2-trichloroethanol, and obtain it in an organic phase. The other phase is aqueous and contains the sulphuric and sulphonic acids. However, the Applicant has found that it was very simple to use chlorobenzene. Thus, only a single solvent is used throughout the process of the invention.

The procedure in step (f) is known per se. The chlorobenzene recovered may be recycled at any point in the process where it is used, for example to (a), to step (e) or for washing the aqueous phase of step (b).

It would not beyond the scope of the invention if only a portion of the aqueous phases obtained in steps (b) and (e) were subjected to step (f) and these acid phases were recycled to steps (a) and (d).

Those skilled in the art way adjust the amount of acid aqueous phase to be subjected to step (f) as a function of the performance obtained in the process of the invention.

The advantage of the dicofol synthesis according to the invention is that a crystallisation and melting operation of industrial grade DDT is avoided. The crystallisation operation is difficult because DDT first passes through a honey-like phase. It is carried out on a metal belt, which is an unhealthy technique and which is a source of pollution. Moreover, the transport of a dangerous material (DDT) is avoided. In addition, this process makes it possible to have a single aromatic compound, chlorobenzene, which acts:
  as reagent and solvent in the condensation reaction of chloral and chlorobenzene; and
  as solvent in the dicofol synthesis.
In fact, the addition of chlorobenzene is useful at the end of the hydrolysis reaction of step (d) in order to permit settling and separation of the organic phase and acid phase.

EXAMPLE 1

Preparation of 1,1-bis(chlorophenyl)-2,2,2-trichloroethanol

Process according to the invention.

430 kg of chloral are dissolved in 770 kg of monochlorobenzene, 305 kg of residual acid from a preceding operation are added and the mixture is cooled to −2° C. 960 kg of 22% oleum are run in in the course of 14 h. The temperature, when all of the oleum has run in, is 20° C. 138 kg of monochlorobenzene are added and the reaction is continued for a further 4 h, allowing the temperature to rise from 20° up to 40° C.

After the addition of 287 kg of monochlorobenzene, stirring is stopped and after leaving to stand for 1 h at 40° C. the acid phase, which is in the lower portion, is drawn off and is subjected to an extraction with 120 kg of monochlorobenzene. 1,500 kg of residual acid are obtained, of which 305 kg will be charged into the following operation, 195 kg reserved for the synthesis of 1,1-bis(chlorophenyl)-2,2,2-trichloroethanol and the remainder, 1,000 kg, also reserved for its desulphonation. The composition of this residual acid is: sulphuric acid 59%; p-chlorobenzenesulphonic acid 36%; and water 4%.

The organic phase, consisting of 1,1-bis(chlorophenyl)-2,2,2-trichlorethane and monochlorobenzene, combined with the monochlorobenzene used for extraction of the residual acid, are washed 3 times with 300 kg of water. 20 kg of sodium carbonate are added to the final washing. The monochlorobenzene is then removed by steam distillation at 110° C. 389 kg of monochlorobenzene are recovered.

The 1,1-bis(chlorophenyl)-2,2,2-trichloroethane obtained, in the liquid state, is then added to the basic aqueous phase from a preceding dehydrochlorination operation and dehydrochlorination is initiated by the addition of 5 kg of dimethylbenzyllaurylammonium chloride, while continuing vigorous stirring for 4 h at 100° C. After standing for 1 h, the aqueous phase is separated off, 318 kg of 50% sodium hydroxide are added and the dehydrochlorination is continued with stirring at 100° C. for 10 h. After dilution with 560 kg of water and standing for 1 h, the organic phase is drawn off and the aqueous phase is retained for the following operation. The organic phase is then washed 3 times with 250 kg of a 1N sulphuric acid solution and 888 kg of 1,1-bis(chlorophenyl)-2,2-dichloroethylene are obtained.

The 1,1-bis(chlorophenyl)-2,2-dichloroethylene is subjected to bulk chlorination, using gaseous chlorine, at 90°–100° C., from mercury vapour lamps and the discontinuous incorporation of 3 kg of azobisisobutyronitrile. The total chlorine introduced is 440 kg, of which 235 kg react. After degassing with nitrogen, 1,072 kg of 1,1-bis(chlorophenyl)-1,2,2,2-tetrachloroethane are obtained.

71 kg of water are added to the 1,1-bis(chlorophenyl)-1,2,2,2-tetrachloroethane, in the liquid stage at 90° C., and the mixture is refluxed. Subsequently the 195 kg of residual acid are charged and heating is continued up to 140° C. 100 kg of hydrogen chloride are degassed during the hydrolysis reaction time of 18 h at 140°–150° C. The hydrogen chloride is absorbed with water containing hydrochloric acid. During the reaction, 44 kg of water are added in order to compensate for the consumption during the reaction.

While continuing to stir, 101 kg of monochlorobenzene and 142 kg of water are added. After standing for 1 h, the organic phase is drawn off. The acid phase is washed with 60 kg of monochlorobenzene and, by drawing off, 395 kg of acid phase are separated off, this phase being reserved for its desulphonation.

The monochlorobenzene wash is combined with the organic phase drawn off and the whole is washed 4 times with 240 kg of water. The monochlorobenzene is distilled off by entraining in steam at 110°–120° C. 141 kg of monochlorobenzene and 1,000 kg of 1,1-bis(chlorophenyl)-2,2,2-trichloroethanol are recovered, with a yield of 87/88%.

The 1,000 kg of residual acid reserved for the synthesis of 1,1-bis(chlorophenyl)-2,2,2-trichloroethane are mixed with the 395 kg of the acid phase from the hydrolysis reaction to form 1,1-bis(chlorophenyl)-2,2,2-trichloroethanol and with 30 kg of water. The heat evolved causes the temperature of the mixture to rise to 150° C., the mixture is heated up to 180° C. and steam is introduced. The monochlorobenzene resulting from the hydrolysis reaction of p-chlorobenzenesulphonic acid is entrained in steam and washed with a dilute (3%) sodium hydroxide solution. 205 kg of monochlorobenzene are recovered. The final reaction temperature is 205° C.

All of the monochlorobenzene recovered throughout the process is directly recyclable without having to be purified.

EXAMPLE 2

Preparation of 1,1-bis(chlorophenyl)-2,2,2-trichloroethanol

Process not according to the invention.

473 kg of chloral are dissolved in 889 kg of monochlorobenzene. 981 kg of 22% oleum are run in in the course of 1 h 15 min, allowing the temperature to rise from −2° C. up to 15° C. 181 kg of monochlorobenzene are added and the reaction is continued for a further 4 h at 15° C. 165 kg of monochlorobenzene are added and the mixture is heated at 60° C. for 6 h.

After standing for 1 h at 60° C., the acid phase, which is in the lower part, is drawn off and is subjected to extraction with 150 kg of monochlorobenzene. 1,200 kg of residual acid having the following composition ar obtained: sulphuric acid 57%; p-chlorobenzenesulphonic acid 37% and water 5%. This residual acid is desulphonated at 180°–205° C. by introducing steam. 212 kg are recovered, which, after washing with a dilute (3%) sodium hydroxide solution, are recycled.

The organic phase, consisting of 1,1-bis(chlorophenyl)-2,2,2-trichloroethane and monochlorobenzene, combined with the monochlorobenzene used for extraction of the residual acid, is washed 3 times with 350 kg of water. 20 kg of sodium carbonate are added to the final wash. The monochlorobenzene is then separated off by steam distillation at 110° C. 370 kg of monochlorobenzene are recovered.

The molten 1,1-bis(chlorophenyl)-2,2,2-trichloroethane is then solidified, giving 990 kg.

990 kg of 1,1-bis(chlorophenyl)-2,2,2-trichloroethane in solid form are charged into the basic aqueous phase from a previous dehydrochlorination operation. Charging is carried out over a period of 2 h in order to prevent the formation of solid masses inside the reactor. 5 kg of dimethylbenzyllaurylammonium chloride are added, while continuing vigorous stirring for 4 h at 100° C. After standing for 1 h, the aqueous phase is separated off and 318 kg of 50% sodium hydroxide are added and the dehydrochlorination is continued, with stirring, at 100° C. for 10 h. After dilution with 560 kg of water and standing for 1 h, the organic phase is drawn off and the aqueous phase is retained for the following operation. The organic phase is then washed 3 time with 250 kg of a 1N sulphuric acid solution and 888 kg of 1,1-bis(chlorophenyl)-2,2-dichloroethylene are obtained.

The 1,1-bis(chlorophenyl)-2,2-dichloroethylene is subjected to bulk chlorination, with gaseous chlorine, at 90°–100° C., from mercury vapour lamps, and the discontinuous incorporation of 3 kg of azobisisobutyronitrile. The total chlorine introduced is 440 kg, of which 235 kg react. After degassing with nitrogen, 1,072 kg of 1,1-bis(chlorophenyl)-1,2,2,2-tetrachloroethane are obtained.

71 kg of water are added to the 1,1-bis(chlorophenyl)-1,2,2,2-tetrachloroethane, in the liquid state at 90° C., and the mixture is refluxed. 195 kg of a mixture of sulphuric acid, 60.5%; p-chlorobenzenesulphonic acid, 35%; and water 45%, obtained by reacting 98% sulphuric acid and monochlorobenzene at 100° C., are then charged. Heating is continued up to 140° C. 100 kg of hydrogen chloride are released during the hydrolysis reaction time of 18 h at 140°–155° C. The hydrogen chloride is absorbed in water containing hydrochloric acid. In the course of the reaction, 44 kg of water are added in order to compensate for the consumption during the reaction.

While continuing to stir, 101 kg of monochlorobenzene and 42 kg of water are added. After standing for 1 h, the organic phase is drawn off. The acid phase is washed with 60 kg of monochlorobenzene.

The monochlorobenzene wash is combined with the organic phase drawn off and the whole is washed 4 times with 240 kg of water. The monochlorobenzene is distilled off by entraining in steam, at 110°–120° C. 141 kg of monochlorobenzene and 1,000 kg of 1,1-bis(chlorophenyl)-2,2,2-trichloroethanol are recovered, with a yield of 85–86%.

We claim:

1. A process for the synthesis of 1,1-bis(chlorophenyl)-2,2,2-trichloroethanol comprising,
   (i) reacting chloral with an excess of chlorobenzene in the presence of sulfuric acid, which yields an organic phase containing 1,1-bis(chlorophenyl)-2,2,2-trichloroethane and an aqueous acid phase,
   (ii) separating said 1,1-bis(chlorophenyl)-2,2,2-trichloroethane from said organic phase such that said 1,1-bis(chlorophenyl)-2,2,2-trichloroethane is obtained in the molten form,
   (iii) converting said molten 1,1-bis(chlorophenyl)-2,2,2-trichloroethane obtained in step (i) to 1,1-bis(chlorophenyl)-1,2,2,2-tetrachloroethane, and
   (iv) hydrolyzing said 1,1-bis(chlorophenyl)-1,2,2,2-tetrachloroethane to obtain a solution containing 1,1-bis(chlorophenyl)-2,2,2-trichloroethanol.

2. A process for the synthesis of 1,1-bis(chlorophenyl)-2,2,2-trichloroethanol according to claim 1, comprising, a further step (v) wherein, chlorobenzene is added to the reaction mixture subsequent to said hydrolyzing step.

3. A process for the synthesis of 1,1-bis(chlorophenyl)-2,2,2-trichloroethanol according to claim 1, wherein, said 1,1-bis(chlorophenyl)-2,2,2-trichloroethane used in step (iii) is not initially in the solid state.

4. A process for the synthesis of 1,1-bis(chlorophenyl)-2,2,2-trichloroethanol according to claim 1 wherein, said hydrolyzing step is conducted in the presence of said aqueous acid phase of step (i).

5. A process for the synthesis of 1,1-bis(chlorophenyl)-2,2,2-trichloroethanol according to claim 3 wherein, said chlorobenzene used in step (i) is separated and recycled to be used in step (i).

6. A process for the synthesis of 1,1-bis(chlorophenyl)-2,2,2-trichloroethanol according to claim 4 wherein, said chlorobenzene added in step (b) is separated and recycled to said step (i).

7. A process for the synthesis of 1,1-bis(chlorophenyl)-2,2,2-trichloroethanol according to claim 4 wherein, said chlorobenzene added in step (v) is separated from the products of step (iv) and recycled to be used again in step (v).

8. A process for the synthesis of 1,1-bis(chlorophenyl)-2,2,2-trichloroethanol according to claim 4 wherein, said chlorobenzene added in step (i) is separated from the products of step (i) and recycled to be used in step (v).

9. A process for the synthesis of 1,1-bis(chlorophenyl)-2,2,2-trichloroethanol comprising,
 (i) reacting chloral with an excess of chlorobenzene in the presence of sulfuric acid, which yields an organic phase containing 1,1-bis (chlorophenyl)-2,2,2-trichloroethane and an aqueous acid phase,
 (ii) converting the 1,1-bis(chlorophenyl)-2,2,2-trichloroethane obtained in step (i) to 1,1-bis(chlorophenyl)-1,2,2,2-tetrachloroethane, and
 (iii) hydrolyzing said 1,1-bis(chlorophenyl)-1,2,2,2-trichloroethane to obtain a solution containing 1,1-bis(chlorophenyl)-2,2,2-tetrachloroethanol,
 with said aqueous acid phase of step (i) being used in said hydrolyzing step.

10. A process for the synthesis of 1,1-bis(chlorophenyl)-2,2,2-trichloroethanol comprising,
 (i) reacting chloral with an excess of chlorobenzene in the presence of sulfuric acid, which yields an organic phase containing 1,1-bis(chlorophenyl)-2,2,2-trichloroethane and an aqueous acid phase,
 (ii) converting the 1,1-bis(chlorophenyl)-2,2,2-trichloroethane obtained in step (i) to 1,1-bis(chlorophenyl)-1,2,2,2-tetrachloroethane, and
 (iii) hydrolyzing said 1,1-bis(chlorophenyl)-1,2,2,2-tetrachloroethane to obtain a solution containing 1,1-bis(chlorophenyl)-2,2,2-trichloroethanol,
 (iv) adding chlorobenzene to said solution containing 1,1-bis(chlorophenyl)-2,2,2-trichloroethanol.

11. A process for the synthesis of 1,1-bis(chlorophenyl)-2,2,2-trichloroethanol comprising,
 (i) reacting chloral with an excess of chlorobenzene in the presence of sulfuric acid, which yields an organic phase containing 1,1-bis(chlorophenyl)-2,2,2-trichloroethane and an aqueous acid phase,
 (ii) converting the 1,1-bis(chlorophenyl)-2,2,2-trichloroethane obtained in step (i) to 1,1-bis(chlorophenyl)-1,2,2,2-tetrachloroethane without crystallizing and melting said 1,1-bis(chlorophenyl)-2,2,2-trichloroethane, and
 (iii) hydrolyzing said 1,1-bis(chlorophenyl)-1,2,2,2-tetrachloroethane to obtain a solution containing 1,1-bis(chlorophenyl)-2,2,2-trichloroethanol.

* * * * *